United States Patent [19]

Miyazawa et al.

[11] Patent Number: 5,202,457
[45] Date of Patent: Apr. 13, 1993

[54] OPTICALLY ACTIVE ALKYL 3-ARYL-3-HYDROXYPROPIONATES AND A METHOD FOR PRODUCING THEREOF

[75] Inventors: Kazutoshi Miyazawa; Naoyuki Yoshida, both of Ichihara, Japan

[73] Assignee: Chisso Corporation, Osaka, Japan

[21] Appl. No.: 920,526

[22] Filed: Jul. 28, 1992

Related U.S. Application Data

[62] Division of Ser. No. 682,111, Apr. 8, 1991, abandoned.

[30] Foreign Application Priority Data

Dec. 4, 1990 [JP] Japan .................... 2-95004
Dec. 4, 1990 [JP] Japan .................... 2-95005

[51] Int. Cl.$^5$ .............................................. C07C 69/76
[52] U.S. Cl. ........................................ 560/60; 435/146
[58] Field of Search ......................... 560/60; 435/146

[56] References Cited

U.S. PATENT DOCUMENTS

4,002,660  1/1977  Snyder, Jr. ................ 558/252
5,066,826  11/1991  Nohira et al. ................ 560/60

FOREIGN PATENT DOCUMENTS

0321918  6/1989  European Pat. Off.
0334966  10/1989  European Pat. Off.
421472   10/1991  European Pat. Off.
1040735   9/1966  United Kingdom.

OTHER PUBLICATIONS

CA 94 (23) 188352j 1981.
CA 89 (3) 24204h 1978.
Wang et al., Tetrahedron Letters, vol. 30, No. 15, pp. 1917–1920 (1989).
Santaniello et al., Chem. Abstracts, vol. 113 (1990) Abstract No. 23293p.
Soai et al., J. Chem. Soc. Chem. Commun. (1985), pp. 138–139.

*Primary Examiner*—Paul J. Killos
*Attorney, Agent, or Firm*—Wenderoth, Lind & Ponack

[57] ABSTRACT

The invention relates to optically active alkyl 3-aryl-3-hydroxypropionates represented by the general formula:

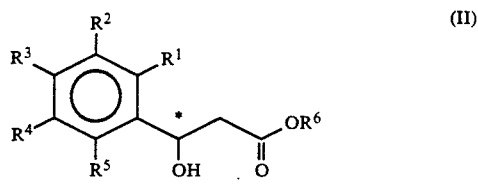

(II)

wherein $R^1$, $R^2$, $R^3$, $R^4$ and $R^5$ are hydrogen, hydroxyl, alkoxy of 1-4 carbon atoms, benzyloxy, flurorine, chlorine or bromine and $R^6$ is alkyl, and a method for producing the above compounds.

2 Claims, No Drawings

OPTICALLY ACTIVE ALKYL 3-ARYL-3-HYDROXYPROPIONATES AND A METHOD FOR PRODUCING THEREOF

This application is a division of now abandoned application Ser. No. 07/682,111, filed Apr. 8, 1991 now abandoned.

BACKGROUND OF THE INVENTION

The present invention relates to optically active alkyl 3-aryl-3-hydroxypropionates represented by the general formula:

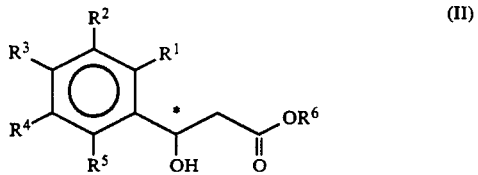

wherein $R^1$, $R^2$, $R^3$, $R^4$ and $R^5$ are hydrogen, hydroxyl, alkoxy of 1–4 carbon atoms, benzyloxy, fluorine, chlorine or bromine and $R^6$ is alkyl, and a method for producing the above compounds.

Optically active alkyl 3-aryl-3-hydroxypropionates represented by the above formula (II) are new compounds which are synthesized by the inventors of the present invention.

The new compounds are useful as starting materials for asymmetric synthesis of biologically and pharmacologically active materials.

It is known that in the optically active alkyl 3-aryl-3-hydroxypropionates, ethyl 3-phenyl-3-hydroxypropionate and ethyl 3-(4-methoxyphenyl)-3-hydroxypropionate are obtained by a method of Mukaiyama et al. (Chem. Lett., 813(1985)) in which ketoester is asymmetrically reduced by using diamine, a method of Soul et al. (J. Am. Chem. Soc., 86, 725(1964)) in which a compound is resolved by kinetics with hydrolytic enzyme, and a method of Santaniero et al. (J. Chem. Soc., Perkin Trans. 1, 1987, 2753) in which asymmetric reduction using baker's yeast is mentioned. However, the compounds obtained by these methods have low purity, and the methods are not desirable industrially and effectively.

In other words, in the method of Mukaiyama et al., namely in the asymmetrical reduction of ketoester with diamine, the compound obtained has low purity (44%ee). The reduction is rather impractical because of the reaction conditions at a low temperature, e.g. −100° C.

The advantage of hydrolysis using enzyme is that (−)- and (+)-enantiomers are obtained. However, in the mass production, there are difficult problems such as selection of a reaction solvent, immobilization of enzyme, and purification of the product. The product do not have enough optical purity (about 70%ee).

Moreover, the asymmetric reduction using Baker's yeast is troublesome and the product has low purity (about 60%ee).

For the above reasons, it is desired to develop a technique for obtaining both enantiomers of optically active alkyl 3-aryl-3-hydroxypropionates useful for common asymmetric synthesis.

SUMMARY OF THE INVENTION

The inventors of the present invention carried out research for obtaining efficiently optically active alkyl 3-aryl-3-hydroxypropionates in large quantities. They have found a method for producing in large quantities optically active alkyl 3-aryl-3-hydroxypropionates.

The present invention provides a method for producing an optically active alkyl 3-aryl-3-hydroxypropionate which comprises reacting in the presence of esterase produced by a micro-organism or esterase obtained from an animal, a triglyceride or a fatty acid vinyl ester with an alkyl 3-aryl-3-hydroxypropionate represented by the general formula:

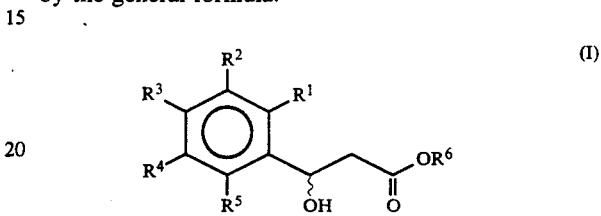

wherein $R^1$, $R^2$, $R^3$, $R^4$ and $R^5$ are hydrogen, hydroxyl, alkoxy of 1–4 carbon atoms, benzyloxy, fluorine, chlorine or bromine and $R^6$ is alkyl, to effect a transesterification reaction, and resolving to an optically active alkyl 3-aryl-3-hydroxypropionate represented by the general formula:

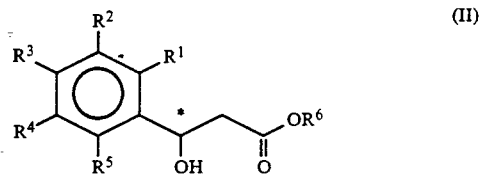

wherein $R^1$, $R^2$, $R^3$, $R^4$, $R^5$ and $R^6$ have the same meanings as described above, and an optically active alkyl 3-aryl-3-acyloxypropionate.

Further, the present invention provides an optically active alkyl 3-aryl-3-hydroxypropionate represented by the general formula:

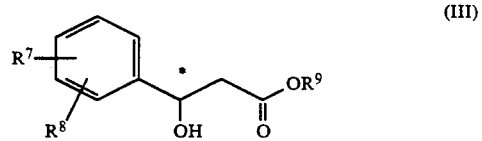

wherein $R^7$ and $R^8$ are hydroxyl, alkoxy of 1–4 carbon atoms, benzyloxy, fluorine, chlorine, or bromine and $R^9$ is alkyl.

DETAILED DESCRIPTION OF THE INVENTION

The following compounds are representative optically active alkyl 3-aryl-3-hydroxypropionates (II) which are obtained by the present invention:

(−)-methyl 3-(2-methoxyphenyl)-3-hydroxypropionate,
(−)-ethyl 3-(2-methoxyphenyl)-3-hydroxypropionate,
(−)-propyl 3-(2-methoxyphenyl)-3-hydroxypropionate,
(−)-butyl 3-(2-methoxyphenyl)-3-hydroxypropionate,
(−)-t-butyl 3-(2-methoxyphenyl)-3-hydroxypropionate, (+)-ethyl 3-(2-methoxyphenyl)-3-hydroxypropionate,
(+)-propyl 3-(2-methoxyphenyl)-3-hydroxypropionate,
(+)-butyl 3-(2-methoxyphenyl)-3-hydroxypropionate,
(+)-t-butyl 3-(2-methoxyphenyl)-3-hydroxypropionate,
(−)-methyl 3-(3-methoxyphenyl)-3-hydroxypropionate,
(−)-ethyl 3-(3-methoxyphenyl)-3-hydroxypropionate,
(−)-propyl 3-(3-methoxyphenyl)-3-hydroxypropionate,
(−)-butyl 3-(3-methoxyphenyl)-3-hydroxypropionate,
(−)-t-butyl 3-(3-methoxyphenyl)-3-hydroxypropionate,
(+)-ethyl 3-(3-methoxyphenyl)-3-hydroxypropionate,
(+)-propyl 3-(3-methoxyphenyl)-3-hydroxypropionate,
(+)-butyl 3-(3-methoxyphenyl)-3-hydroxypropionate,
(+)-t-butyl 3-(3-methoxyphenyl)-3-hydroxypropionate,
(−)-methyl 3-(2,4-dimethoxyphenyl)-3-hydroxypropionate,
(−)-ethyl 3-(2,4-dimethoxyphenyl)-3-hydroxypropionate,
(−)-propyl 3-(2,4-dimethoxyphenyl)-3-hydroxypropionate,
(−)-butyl 3-(2,4-dimethoxyphenyl)-3-hydroxypropionate,
(−)-t-butyl 3-(2,4-dimethoxyphenyl)-3-hydroxypropionate,
(+)-ethyl 3-(2,4-dimethoxyphenyl)-3-hydroxypropionate,
(+)-propyl 3-(2,4-dimethoxyphenyl)-3-hydroxypropionate,
(+)-butyl 3-(2,4-dimethoxyphenyl)-3-hydroxypropionate,
(+)-t-butyl 3-(2,4-dimethoxyphenyl)-3-hydroxypropionate,
(−)-methyl 3-(2,5-dimethoxyphenyl)-3-hydroxypropionate,
(−)-ethyl 3-(2,5-dimethoxyphenyl)-3-hydroxypropionate,
(−)-propyl 3-(2,5-dimethoxyphenyl)-3-hydroxypropionate,
(−)-butyl 3-(2,5-dimethoxyphenyl)-3-hydroxypropionate,
(−)-t-butyl 3-(2,5-dimethoxyphenyl)-3-hydroxypropionate,
(+)-ethyl 3-(2,5-dimethoxyphenyl)-3-hydroxypropionate,
(+)-propyl 3-(2,5-dimethoxyphenyl)-3-hydroxypropionate,
(+)-butyl 3-(2,5-dimethoxyphenyl)-3-hydroxypropionate,
(+)-t-butyl 3-(2,5-dimethoxyphenyl)-3-hydroxypropionate,
(−)-methyl 3-(3,5-dimethoxyphenyl)-3-hydroxypropionate,
(−)-ethyl 3-(3,5-dimethoxyphenyl)-3-hydroxypropionate,
(−)-propyl 3-(3,5-dimethoxyphenyl)-3-hydroxypropionate,
(−)-butyl 3-(3,5-dimethoxyphenyl)-3-hydroxypropionate,
(−)-t-butyl 3-(3,5-dimethoxyphenyl)-3-hydroxypropionate,
(+)-ethyl 3-(3,5-dimethoxyphenyl)-3-hydroxypropionate,
(+)-propyl 3-(3,5-dimethoxyphenyl)-3-hydroxypropionate,
(+)-butyl 3-(3,5-dimethoxyphenyl)-3-hydroxypropionate,
(+)-t-butyl 3- 3,5-dimethoxyphenyl)-3-hydroxypropionate,
(−)-methyl 3-(3,4-dimethoxyphenyl)-3-hydroxypropionate,
(−)-ethyl 3-(3,4-dimethoxyphenyl)-3-hydroxypropionate,
(−)-propyl 3-(3,4-dimethoxyphenyl)-3-hydroxypropionate,
(−)-butyl 3-(3,4-dimethoxyphenyl)-3-hydroxypropionate,
(−)-t-butyl 3-(3,4-dimethoxyphenyl)-3-hydroxypropionate,
(+)-ethyl 3-(3,4-dimethoxyphenyl)-3-hydroxypropionate,
(+)-propyl 3-(3,4-dimethoxyphenyl)-3-hydroxypropionate,
(+)-butyl 3-(3,4-dimethoxyphenyl)-3-hydroxypropionate,
(+)-t-butyl 3-(3,4-dimethoxyphenyl)-3-hydroxypropionate,
(−)-methyl 3-(2-benzyloxyphenyl)-3-hydroxypropionate,
(−)-ethyl 3-(2-benzyloxyphenyl)-3-hydroxypropionate,
(−)-propyl 3-(2-benzyloxyphenyl)-3-hydroxypropionate,
(−)-butyl 3-(2-benzyloxyphenyl)-3-hydroxypropionate,
(−)-t-butyl 3-(2-benzyloxyphenyl)-3-hydroxypropionate,
(+)-methyl 3-(2-benzyloxyphenyl)-3-hydroxypropionate,
(+)-ethyl 3-(2-benzyloxyphenyl)-3-hydroxypropionate,
(+)-propyl 3-(2-benzyloxyphenyl)-3-hydroxypropionate,
(+)-butyl 3-(2-benzyloxyphenyl)-3-hydroxypropionate,
(+)-t-butyl 3-(2-benzyloxyphenyl)-3-hydroxypropionate,
(−)-methyl 3-(3-benzyloxyphenyl)-3-hydroxypropionate,
(−)-ethyl 3-(3-benzyloxyphenyl)-3-hydroxypropionate,
(−)-propyl 3-(3-benzyloxyphenyl)-3-hydroxypropionate,
(−)-butyl 3-(3-benzyloxyphenyl)-3-hydroxypropionate,
(−)-t-butyl 3-(3-benzyloxyphenyl)-3-hydroxypropionate,
+)-methyl 3-(3-benzyloxyphenyl)-3-hydroxypropionate,
(+)-ethyl 3-(3-benzyloxyphenyl)-3-hydroxypropionate,
(+)-propyl 3-(3-benzyloxyphenyl)-3-hydroxypropionate,
(+)-butyl 3-(3-benzyloxyphenyl)-3-hydroxypropionate,
(+)-t-butyl 3-(3-benzyloxyphenyl)-3-hydroxypropionate,
(−)-methyl 3-(4-benzyloxyphenyl)-3-hydroxypropionate,
(−)-ethyl 3-(4-benzyloxyphenyl)-3-hydroxypropionate,
(−)-propyl 3-(4-benzyloxyphenyl)-3-hydroxypropionate,
(−)-butyl 3-(4-benzyloxyphenyl)-3-hydroxypropionate,
(−)-t-butyl 3-(4-benzyloxyphenyl)-3-hydroxypropionate,
(+)-methyl 3-(4-benzyloxyphenyl)-3-hydroxypropionate,
(+)-ethyl 3-(4-benzyloxyphenyl)-3-hydroxypropionate,
(+)-propyl 3-(4-benzyloxyphenyl)-3-hydroxypropionate,
(+)-butyl 3-(4-benzyloxyphenyl)-3-hydroxypropionate,
(+)-t-butyl 3-(4-benzyloxyphenyl)-3-hydroxypropionate,
(−)-methyl 3-(2-fluorophenyl)-3-hydroxypropionate,
(−)-ethyl 3-(2-fluorophenyl)-3-hydroxypropionate, (−)-propyl 3-(2-fluorophenyl)-3-hydroxypropionate,
(−)-butyl 3-(2-fluorophenyl)-3-hydroxypropionate,
(−)-t-butyl 3-(2-fluorophenyl)-3-hydroxypropionate,
(+)-methyl 3-(2-fluorophenyl)-3-hydroxypropionate,
(+)-ethyl 3-(2-fluorophenyl)-3-hydroxypropionate,
(+)-propyl 3-(2-fluorophenyl)-3-hydroxypropionate,
(+)-butyl 3-(2-fluorophenyl)-3-hydroxypropionate,
(+)-t-butyl 3-(2-fluorophenyl)-3-hydroxypropionate,
(−)-methyl 3-(3-fluorophenyl)-3-hydroxypropionate,
(−)-ethyl 3-(3-fluorophenyl)-3-hydroxypropionate,
(−)-propyl 3-(3-fluorophenyl)-3-hydroxypropionate,
(−)-butyl 3-(3-fluorophenyl)-3-hydroxypropionate,
(−)-t-butyl 3-(3-fluorophenyl)-3-hydroxypropionate,
(+)-methyl 3-(4-fluorophenyl)-3-hydroxypropionate,
(+)-ethyl 3-(4-fluorophenyl)-3-hydroxypropionate,
(+)-propyl 3-(4-fluorophenyl)-3-hydroxypropionate,
(+)-butyl 3-(4-fluorophenyl)-3-hydroxypropionate,
(+)-t-butyl 3-(4-fluorophenyl)-3-hydroxypropionate,
(−)-methyl 3-(2,3-difluorophenyl)-3-hydroxypropionate,
(−)-ethyl 3-(2,3-difluorophenyl)-3-hydroxypropionate,
(−)-propyl 3-(2,3-difluorophenyl)-3-hydroxypropionate,
(−)-butyl 3-(2,3-difluorophenyl)-3-hydroxypropionate,
(−)-t-butyl 3-(2,3-difluorophenyl)-3-hydroxypropionate,
(+)-methyl 3-(2,3-difluorophenyl)-3-hydroxypropionate,
(+)-ethyl 3-(2,3-difluorophenyl)-3-hydroxypropionate,
(+)-propyl 3-(2,3-difluorophenyl)-3-hydroxypropionate,
(+)-butyl 3-(2,3-difluorophenyl)-3-hydroxypropionate,
(+)-t-butyl 3-(2,3-difluorophenyl)-3-hydroxypropionate,
(−)-methyl 3-(3,4-difluorophenyl)-3-hydroxypropionate,
(−)-ethyl 3-(3,4-difluorophenyl)-3-hydroxypropionate,
(−)-propyl 3-(3,4-difluorophenyl)-3-hydroxypropionate,
(−)-butyl 3-(3,4-difluorophenyl)-3-hydroxypropionate,
(−)-t-butyl 3-(3,4-difluorophenyl)-3-hydroxypropionate,
(+)-methyl 3-(3,4-difluorophenyl)-3-hydroxypropionate,
(+)-ethyl 3-(3,4-difluorophenyl)-3-hydroxypropionate,
(+)-propyl 3-(3,4-difluorophenyl)-3-hydroxypropionate,
(+)-butyl 3-(3,4-difluorophenyl)-3-hydroxypropionate,
(+)-t-butyl 3-(3,4-difluorophenyl)-3-hydroxypropionate,
(−)-methyl 3-(3,5-difluorophenyl)-3-hydroxypropionate,
(−)-ethyl 3-(3,5-difluorophenyl)-3-hydroxypropionate,
(−)-propyl 3-(3,5-difluorophenyl)-3-hydroxypropionate,
(−)-butyl 3-(3,5-difluorophenyl)-3-hydroxypropionate,
(−)-t-butyl 3-(3,5-difluorophenyl)-3-hydroxypropionate,
(+)-methyl 3-(3,5-difluorophenyl)-3-hydroxypropionate,
(+)-ethyl 3-(3,5-difluorophenyl)-3-hydroxypropionate,
(+)-propyl 3-(3,5-difluorophenyl)-3-hydroxypropionate,
(+)-butyl 3-(3,5-difluorophenyl)-3-hydroxypropionate,
(+)-t-butyl 3-(3,5-difluorophenyl)-3-hydroxypropionate,
(−)-methyl 3-(2-chlorophenyl)-3-hydroxypropionate,
(−)-ethyl 3-(2-chlorophenyl)-3-hydroxypropionate,
(−)-propyl 3-(2-chlorophenyl)-3-hydroxypropionate,
(−)-butyl 3-(2-chlorophenyl)-3-hydroxypropionate,
(−)-t-butyl 3-(2-chlorophenyl)-3-hydroxypropionate,
(+)-methyl 3-(2-chlorophenyl)-3-hydroxypropionate,
(+)-ethyl 3-(2-chlorophenyl)-3-hydroxypropionate,
(+)-propyl 3-(2-chlorophenyl)-3-hydroxypropionate,
(+)-butyl 3-(2-chlorophenyl)-3-hydroxypropionate,
(+)-t-butyl 3-(2-chlorophenyl)-3-hydroxypropionate,
(−)-methyl 3-(3-chlorophenyl)-3-hydroxypropionate,
(−)-ethyl 3-(3-chlorophenyl)-3-hydroxypropionate,
(−)-propyl 3-(3-chlorophenyl)-3-hydroxypropionate,
(−)-butyl 3-(3-chlorophenyl)-3-hydroxypropionate,
(−)-t-butyl 3-(3-chlorophenyl)-3-hydroxypropionate,
(+)-methyl 3-(3-chlorophenyl)-3-hydroxypropionate,
(+)-ethyl 3-(3-chlorophenyl)-3-hydroxypropionate,
(+)-propyl 3-(3-chlorophenyl)-3-hydroxypropionate,
(+)-butyl 3-(3-chlorophenyl)-3-hydroxypropionate,
(+)-t-butyl 3-(3-chlorophenyl)-3-hydroxypropionate,
(−)-methyl 3-(4-chlorophenyl)-3-hydroxypropionate,
(−)-ethyl 3-(4-chlorophenyl)-3-hydroxypropionate,
(−)-propyl 3-(4-chlorophenyl)-3-hydroxypropionate,
(−)-butyl 3-(4-chlorophenyl)-3-hydroxypropionate,
(−)-t-butyl 3-(4-chlorophenyl)-3-hydroxypropionate,
(+)-methyl 3-(4-chlorophenyl)-3-hydroxypropionate,
(+)-ethyl 3-(4-chlorophenyl)-3-hydroxypropionate,
(+)-propyl 3-(4-chlorophenyl)-3-hydroxypropionate,
(+)-butyl 3-(4-chlorophenyl)-3-hydroxypropionate,
(+)-t-butyl 3-(4-chlorophenyl)-3-hydroxypropionate,
(−)-methyl 3-(2,3-dichlorophenyl)-3-hydroxypropionate,
(−)-ethyl 3-(2,3-dichlorophenyl)-3-hydroxypropionate,
(−)-propyl 3-(2,3-dichlorophenyl)-3-hydroxypropionate,
(−)-butyl 3-(2,3-dichlorophenyl)-3-hydroxypropionate,
(−)-t-butyl 3-(2,3-dichlorophenyl)-3-hydroxypropionate,
(+)-methyl 3-(2,3-dichlorophenyl)-3-hydroxypropionate,
(+)-ethyl 3-(2,3-dichlorophenyl)-3-hydroxypropionate,
(+)-propyl 3-(2,3-dichlorophenyl)-3-hydroxypropionate,
(+)-butyl 3-(2,3-dichlorophenyl)-3-hydroxypropionate,
(+)-t-butyl 3-(2,3-dichlorophenyl)-3-hydroxypropionate,
(−)-methyl 3-(3,4-dichlorophenyl)-3-hydroxypropionate,
(−)-ethyl 3-(3,4-dichlorophenyl)-3-hydroxypropionate,
(−)-propyl 3-(3,4-dichlorophenyl)-3-hydroxypropionate,
(−)-butyl 3-(3,4-dichlorophenyl)-3-hydroxypropionate,
(−)-t-butyl 3-(3,4-dichlorophenyl)-3-hydroxypropionate,
(+)-methyl 3-(3,4-dichlorophenyl)-3-hydroxypropionate,
(+)-ethyl 3-(3,4-dichlorophenyl)-3-hydroxypropionate,
(+)-propyl 3-(3,4-dichlorophenyl)-3-hydroxypropionate,
(+)-butyl 3-(3,4-dichlorophenyl)-3-hydroxypropionate,
(+)-t-butyl 3-(3,4-dichlorophenyl)-3-hydroxypropionate,
(−)-methyl 3-(2-bromophenyl)-3-hydroxypropionate,
(−)-ethyl 3-(2-bromophenyl)-3-hydroxypropionate,
(−)-propyl 3-(2-bromophenyl)-3-hydroxypropionate,
(−)-butyl 3-(2-bromophenyl)-3-hydroxypropionate,
(−)-t-butyl 3-(2-bromophenyl)-3-hydroxypropionate,
(+)-methyl 3-(2-bromophenyl)-3-hydroxypropionate,
(+)-ethyl 3-(2-bromophenyl)-3-hydroxypropionate,
(+)-propyl 3-(2-bromophenyl)-3-hydroxypropionate, (+)-butyl 3-(2-bromophenyl)-3-hydroxypropionate,
(−)-methyl 3-(3-bromophenyl)-3-hydroxypropionate,
(−)-ethyl 3-(3-bromophenyl)-3-hydroxypropionate,
(−)-propyl 3-(3-bromophenyl)-3-hydroxypropionate,
(−)-butyl 3-(3-bromophenyl)-3-hydroxypropionate,
(−)-t-butyl 3-(3-bromophenyl)-3-hydroxypropionate,
(+)-methyl 3-(3-bromophenyl)-3-hydroxypropionate,
(+)-ethyl 3-(3-bromophenyl)-3-hydroxypropionate,
(+)-propyl 3-(3-bromophenyl)-3-hydroxypropionate,
(+)-butyl 3-(3-bromophenyl)-3-hydroxypropionate,
(+)-t-butyl 3-(3-bromophenyl)-3-hydroxypropionate,
(−)-methyl 3-(4-bromophenyl)-3-hydroxypropionate,
(−)-ethyl 3-(4-bromophenyl)-3-hydroxypropionate,
(−)-propyl 3-(4-bromophenyl)-3-hydroxypropionate,
(−)-butyl 3-(4-bromophenyl)-3-hydroxypropionate,
(−)-t-butyl 3-(4-bromophenyl)-3-hydroxypropionate,
(+)-methyl 3-(4-bromophenyl)-3-hydroxypropionate,
(+)-ethyl 3-(4-bromophenyl)-3-hydroxypropionate,
(+)-propyl 3-(4-bromophenyl)-3-hydroxypropionate,
(+)-butyl 3-(4-bromophenyl)-3-hydroxypropionate,
(+)-t-butyl 3-(4-bromophenyl)-3-hydroxypropionate,
(−)-methyl 3-(2,3-dibromophenyl)-3-hydroxypropionate,
(−)-ethyl 3-(2,3-dibromophenyl)-3-hydroxypropionate,
(−)-propyl 3-(2,3-dibromophenyl)-3-hydroxypropionate,
(−)-butyl 3-(2,3-dibromophenyl)-3-hydroxypropionate,
(−)-t-butyl 3-(2,3-dibromophenyl)-3-hydroxypropionate,
(+)-methyl 3-(2,3-dibromophenyl)-3-hydroxypropionate,
(+)-ethyl 3-(2,3-dibromophenyl)-3-hydroxypropionate,
(+)-propyl 3-(2,3-dibromophenyl)-3-hydroxypropionate,
(+)-butyl 3-(2,3-dibromophenyl)-3-hydroxypropionate,
(+)-t-butyl 3-(2,3-dibromophenyl)-3-hydroxypropionate,
(−)-methyl 3-(3,4-dibromophenyl)-3-hydroxypropionate,
(−)-ethyl 3-(3,4-dibromophenyl)-3-hydroxypropionate,
(−)-propyl 3-(3,4-dibromophenyl)-3-hydroxypropionate,
(−)-butyl 3-(3,4-dibromophenyl)-3-hydroxypropionate,
(−)-t-butyl 3-(3,4-dibromophenyl)-3-hydroxypropionate,
(+)-methyl 3-(3,4-dibromophenyl)-3-hydroxypropionate,
(+)-ethyl 3-(3,4-dibromophenyl)-3-hydroxypropionate,
(+)-propyl 3-(3,4-dibromophenyl)-3-hydroxypropionate,
(+)-butyl 3-(3,4-dibromophenyl)-3-hydroxypropionate,
(+)-t-butyl 3-(3,4-dibromophenyl)-3-hydroxypropionate,
(−)-methyl 3-(3,5-dibromophenyl)-3-hydroxypropionate,
(−)-ethyl 3-(3,5-dibromophenyl)-3-hydroxypropionate,
(−)-propyl 3-(3,5-dibromophenyl)-3-hydroxypropionate,
(−)-butyl 3-(3,5-dibromophenyl)-3-hydroxypropionate,
(−)-t-butyl 3-(3,5-dibromophenyl)-3-hydroxypropionate,
(+)-methyl 3-(3,5-dibromophenyl)-3-hydroxypropionate,
(+)-ethyl 3-(3,5-dibromophenyl)-3-hydroxypropionate,
(+)-propyl 3-(3,5-dibromophenyl)-3-hydroxypropionate,
(+)-butyl 3-(3,5-dibromophenyl)-3-hydroxypropionate,
(+)-t-butyl 3-(3,5-dibromophenyl)-3-hydroxypropionate,
(−)-methyl 3-(3,5-dichlorophenyl)-3-hydroxypropionate,
(−)-ethyl 3-(3,5-dichlorophenyl)-3-hydroxypropionate,
(−)-propyl 3-(3,5-dichlorophenyl)-3-hydroxypropionate,
(−)-butyl 3-(3,5-dichlorophenyl)-3-hydroxypropionate,
(−)-t-butyl 3-(3,5-dichlorophenyl)-3-hydroxypropionate,
(+)-methyl 3-(3,5-dichlorophenyl)-3-hydroxypropionate,
(+)-ethyl 3-(3,5-dichlorophenyl)-3-hydroxypropionate,
(+)-propyl 3-(3,5-dichlorophenyl)-3-hydroxypropionate,
(+)-butyl 3-(3,5-dichlorophenyl)-3-hydroxypropionate,
(+)-t-butyl 3-(3,5-dichlorophenyl)-3-hydroxypropionate and the like.

In this invention, the alkyl 3-aryl-3-hydroxypropionates of the raw materials are easily obtained by reacting an aryl aldehydes with ethyl bromoacetate in the presence of zinc. They are also obtained by the reduction of appropriate arylcarbonylacetate esters.

As for triglycerides in the enzyme reaction, triacetin, tripropionin, tributyrin, tricaproin, trilaurin, etc. can be exemplified, and as for fatty acid vinyl esters, vinyl acetate, vinyl propionate, vinyl butyrate, vinyl caproate, vinyl laurate, etc. can be exemplified. These compounds are commercially available and also easily obtained by synthesis.

The following table shows commercially available esterases that can be used in the present invention.

TABLE

| Trade name | Origin | Seller or Maker |
| --- | --- | --- |
| Lipase PS | Pseudomonas sp. | Amano Pharmaceutical Co., Ltd |
| Lipase CES | Pseudomonas sp. | Amano Pharmaceutical Co., Ltd |
| Lipase AP | Aspergillus niger | Amano Pharmaceutical Co., Ltd |
| Lipase M | Mucor javanicus | Amano Pharmaceutical Co., Ltd |
| Lipase CE | Humicola lanuginosa | Amano Pharmaceutical Co., Ltd |
| Lipase F-AP | Rhizopus javanicus | Amano Pharmaceutical Co., Ltd |
| Lipase II | Porcine pancreas | Sigma Chemical |
| Lipase VIII | Geotrichum candidum | Sigma Chemical |
| Lipase X | Rhizopus delamar | Sigma Chemical |
| Lipase | Chromobacterium viscosum | Toyo Jozo Co., Ltd |
| Lipase A | Aspergillus niger | Novo Industi A/S |
| Lipase | Rhizopus niveus | Nagase Biochemicals, Co. Ltd |
| Lipase B | Pseudomonas fragi | Sapporo Beer Co., Ltd |

In addition to these enzymes, microorganisms which produce the enzymes having the above ability can be used regardless of their species and genus. As such microorganisms, the genera Pseudomonas, Arthrobacter, Acromobacter, Alcaligenes, Asperigillus, Chromobacterium, Candida, Mucor, Rhizopus, etc, can be exemplified.

In these microorganisms, the genus Pseudomonas is more preferable.

The reaction is conducted by mixing an alkyl 3-aryl-3-hydroxypropionate with a fatty acid vinyl ester or a triglyceride, and contacting efficiently the mixture with an enzyme. The reaction temperature is suitably room temperature (about 10° C.) to 150° C., preferably 20° to 45° C. The reaction time is widely variable, say 1 to 1000 hours.

The alkyl 3-aryl-3-hydroxypropionate which is a substrate and the fatty acid vinyl ester or the triglyceride are mixed in the ratio 1:0.5 to 1:10 by mole, and preferably 1:0.5 by mole.

As for a reaction solvent which does not inhibit esterase activities, if necessary, hydrocarbons such as n-hexane, n-heptane, etc., benzene, toluene, ethers and the like can be used. Otherwise, there is no necessity of such solvents.

After the enzyme reaction as described above, the esterase can be removed by conventional filter operation and used again, as it is. The reactant which is the filtrate can be separated into an optically active alkyl 3-aryl-3-hydroxypropionate and an optically active alkyl 3-aryl-3-acyloxypropionate, respectively, for instance by distillation under reduced pressure or column chromatography. After the reaction, when the optical purity of the optically active alkyl 3-aryl-3-hydroxypropionate is low (when the transesterification is not enough), the compound having high optical purity (>99%ee) can be obtained by re-transesterification with the esterase.

The optically active alkyl 3-aryl-3-acyloxypropionates obtained by the above processes are hydrolyzed in an alkali (e. g. potassium hydroxide or sodium hydroxide) or an acid (e. g. hydrochloric acid or sulfuric acid) or alcoholized (in methanol or ethanol) to derive antipodes of the above optically active alkyl 3-aryl-3-hydroxypropionates or optically active 3-aryl-3-hydroxy propionic acid.

By the above processes, the optically active (+)- and (−)-alkyl 3-aryl-3-hydroxypropionates can be obtained. Further, (+)- or (−)-alkyl 3-aryl-3-acyloxypropionates are dependent on the esterases used.

The method of the present invention is excellent in the efficient mass production of new optically active alkyl 3-aryl-3-hydroxypropionates having high optical purities.

The optically active alkyl 3-aryl-3-hydroxypropionates are useful as starting materials for asymmetric synthesis in wide application.

For example, optically active ethyl 3-phenyl-3-hydroxypropionate which is a known compound is reduced to obtain optically active 1-phenyl-1,3-propanediol. The compound obtained is a starting material of fluoxetin which is an antidepressant (J. Am. Chem. Soc., 53, 4081(1988)). Moreover, the compounds obtained by the method of the present invention can be lead to various kinds of materials having biological and pharmacological activity.

DESCRIPTION OF PREFERRED EMBODIMENTS

The following examples illustrate the present invention more specifically.

EXAMPLE 1

The mixture of 5.0 g (25.7 mmol) of ethyl 3-phenyl-3-hydroxypropionate, 1.83 g (13 mmol) of vinyl caproate and 1.0 g of lipase PS was stirred at room temperature for 35 hours. After the lipase was removed by filtration, the filtrate was eluted by column chromatography (eluting solution; 9/1 of toluene/ethyl acetate) to obtain 2.2 g (>99%ee) of (−)-ethyl 3-phenyl-3-hydroxypropionate and 4.1 g (about 90%ee) of (+)-ethyl 3-phenyl-3-hexanoyloxypropionate.

To determine the optical purity, (+)-ethyl 3-phenyl-3-hydroxypropionate which was obtained by alcoholysis of (+)-ethyl 3-phenyl-3-hexanoyloxypropionate in ethanol was used.

The optical purity was determined by the following method: after the optically active compounds were reacted with 4-nitrophenyl isocyanate, the compounds obtained were eluted by HPLC (Japanese Patent Application No. 1-176580).

EXAMPLE 2

The mixture of 4.0 g (21 mmol) of S-ethyl 3-phenyl-3-hydroxypropionate having a low optical purity of 13.3%ee, 2.2 g (15 mmol) of vinyl caproate and 2.0 g of lipase PS was stirred at room temperature for 30 hours. After the lipase was removed by filtration, the filtrate was eluted by column chromatography (eluting solution; 9/1 of toluene/ethyl acetate). 1.7 g (99%ee) of (−)-ethyl 3-phenyl-3-hydroxypropionate having high optical purity and 2.7 g of (+)-ethyl 3-phenyl-3-hexanoyloxy propionate were obtained, respectively.

EXAMPLE 3

The mixture of 5.0 g (28 mmol) of methyl 3-phenyl-3-hydroxypropionate, 1.97 g (14 mmol) of vinyl caproate and 2.0 g of lipase PS was stirred at room temperature for 28 hours. After the lipase was removed by filtration, the filtrate was eluted by column chromatography (eluting solution; 9/1 of toluene/ethyl acetate). 2.35 g (88%ee) of (−)-methyl 3-phenyl-3-hydroxypropionate and 3.97 g (91%ee) of (+)-methyl 3-phenyl-3-hexanoyloxy-propionate were obtained, respectively.

The optical purity of (+)-methyl 3-phenyl-3-hexanoyloxypropionate was determined by using (+)-ethyl 3-phenyl-3-hydroxypropionate obtained by alcoholysis of the former compound in ethanol.

The optical purities of both (+)- and (−)- compounds were determined by the same method as described in Example 1.

EXAMPLE 4

The mixture of 5.0 g of ethyl 3-(4-methoxyphenyl)-3-hydroxypropionate, 1.6 g of vinyl caproate and 2.0 g of lipase PS was stirred at room temperature for 30 hours. After the lipase was removed by filtration, the filtrate was eluted by column chromatography (eluting solution; 3/1 of toluene/ethyl acetate). 3.8 g of (−)-ethyl 3-(4-methoxyphenyl)-3-hydroxypropionate was obtained. The specific rotation of the compound was $[\alpha]_D - 19°$ (c1.22, CHCl$_3$).

EXAMPLE 5

The mixture of 5.0 g (22 mmol) of ethyl 3-(2-methoxyphenyl)-3-hydroxypropionate, 1.6 g (11 mmol) of vinyl caproate and 2.0 g of lipase PS was stirred at room temperature for 3 days. After the lipase was removed by filtration, the filtrate was eluted by column chromatography (eluting solution; 5/1 of toluene/ethyl acetate). 1.9 g (45%ee) of (−)-ethyl 3-(2-methoxyphenyl)-3-hydroxypropionate was obtained. The specific rotation of the compound was $[\alpha]_D^{31}$ −27.1°(c1.05, CHCl$_3$).

Further, 5.4 g of (+)-ethyl 3-(2-methoxyphenyl)-3-hexanoyloxypropionate was obtained. The specific rotation of the compound was $[\alpha]_D^{30}$ +32.0°(c0.20, CHCl$_3$).

To determine optical purity of (+)-ethyl 3-(2-methoxyphenyl)-3-hexanoyloxypropionate, the compound was converted into (+)-3-(2-methoxyphenyl)-

1,3-propanediol with lithium aluminium hydride, and the compound obtained was analyzed with an optical resolution HPLC (Chiral Cel OB, manufactured by Daisel Co.). The result was 74%ee.

EXAMPLE 6

The mixture of 5.0 g (20 mmol) of ethyl 3-(3,4-dimethoxyphenyl)-3-hydroxypropionate, 1.4 g (13 mmol) of vinyl caproate and 1.0 g of lipase PS was stirred at room temperature for 12 days. After the lipase was removed by filtration, the filtrate was eluted by column chromatography (eluting solution; 9/1 of toluene/ethyl acetate) to obtain 2 g (>50%ee) of (−)-ethyl 3-(3,4-dimethoxyphenyl)-3-hydroxypropionate and 4.3 g (about 43%ee) of (+)-ethyl 3-(3,4-dimethoxyphenyl)-3-hexanoyloxypropionate.

The optical purity was determined by the following method: after (−)-ethyl 3-(3,4-dimethoxyphenyl)-3-hydroxypropionate was reacted with 4-nitrophenyl isocyanate, the compounds obtained were eluted by HPLC (Japanese Patent Application No. 1-176580). The specific rotation of the compound was $[\alpha]_D^{21}$ −16.9°(c1.0, CDCL$_3$)

To determine optical purity of (+)-ethyl 3-(3,4-dimethoxyphenyl)-3-hexanoyloxypropionate, the compound was converted into (+)-3-(3,4-dimethoxyphenyl)-1,3-propanediol with lithium aluminium hydride, and the compound obtained was analyzed with an optical resolution HPLC (Chiral Cel OB, manufactured by Daisel Co.).

EXAMPLE 7

The mixture of 5.0 g (20 mmol) of ethyl 3-(2,4-dimethoxyphenyl)-3-hydroxypropionate, 10 ml of vinyl acetate and 2.0 g of lipase PS was stirred at room temperature for 50 days. After the lipase was removed by filtration, the filtrate was eluted by column chromatography (eluting solution; 9/1 of toluene/ethyl acetate) to obtain 3.5 g (35%ee) of (−)-ethyl 3-(2,4-dimethoxyphenyl)-3-hydroxypropionate and 1.5 g of (+)-ethyl 3-(2,4-dimethoxyphenyl)-3-acetoxypropionate, respectively.

The optical purity was determined by the following method: after (−)-ethyl 3-(2,4-dimethoxyphenyl)-3-hydroxypropionate was reacted with 4-nitrophenyl isocyanate, the compounds obtained were eluted by HPLC. The specific rotation of the compound was $[\alpha]_D^{21}$ −12.4°(c1.1, CDCl$_3$).

EXAMPLE 8

The mixture of 5.0 g (20 mmol) of ethyl 3-(3,5-dimethoxyphenyl)-3-hydroxypropionate, 1.4 g (16 mmol) of vinyl acetate and 2.0 g of lipase PS was stirred at room temperature for 8 days. After the lipase was removed by filtration, the filtrate was eluted by column chromatography (eluting solution; 9/1 of toluene/ethyl acetate) to obtain 2.2 g (50%ee) of (−)-ethyl 3-(3,5-dimethoxyphenyl)-3-hydroxypropionate and 2.7 g of (+)-ethyl 3-(3,5-di-methoxyphenyl)-3-acetoxypropionate.

The optical purity was determined by the following method: after (−)-ethyl 3-(3,4-dimethoxyphenyl)-3-hydroxypropionate was reacted with 4-nitrophenyl isocyanate, the compounds obtained were eluted by HPLC. The specific rotation oft eh compound was $[\alpha]_D^{24}$ −11.7° (c1.1, CDCl$_3$).

EXAMPLE 9

The mixture of 5.0 g of ethyl 3-(3-chlorophenyl)-3-hydroxypropionate, 1.6 g of vinyl caproate and 2.0 g of lipase PS was stirred at room temperature for 13 days. After the lipase was removed by filtration, the filtrate was eluted by column chromatography (eluting solution; 9/1 of toluene/ethyl acetate) to obtain 2.34 g (40%ee) of (−)-ethyl 3-(3-chlorophenyl)-3-hydroxypropionate and 2.75 g (>90%ee) of (+)-ethyl 3-(3-chlorophenyl)-3-caproyloxypropionate.

The optical purity was determined by the following method: after (−)-ethyl 3-(3,4-dimethoxyphenyl)-3hydroxypropionate was reacted with 4-nitrophenyl isocyanate, the compounds obtained were eluted by HPLC. To determine the optical purity of the other compound, (+)-ethyl 3-(3-chlorophenyl)-3-acetyloxypropionate, the compound was converted into (+)-3-(3-chlorophenyl) 1,3-propanediol with lithium aluminium hydride, and the compound obtained was analyzed with an optical resolution HPLC (Chiral Cel OB, manufactured by Daisel Co.). The specific rotation of the compound was $[\alpha]_D$ −16.4°(c1.0, CDCl$_3$).

EXAMPLE 10

The mixture of 5.0 g of ethyl 3-(4-chlorophenyl)-3-hydroxypropionate, 1.6 g of vinyl caproate and 2.0 g of lipase PS was stirred at room temperature for 13 days. After the lipase was removed by filtration, the filtrate was eluted by column chromatography (eluting solution; 9/1 of toluene/ethyl acetate) to obtain 2.1 g of (−)-ethyl 3-(4-chlorophenyl)-3-hydroxypropionate and 2.7 g of (+)-ethyl 3-(4-chlorophenyl)-3-caproyloxypropionate, respectively.

The specific rotation of (−)-ethyl 3-(4-chlorophenyl)-3-hydroxypropionate was $[\alpha]_D$−20.2°(c1.0, CDCl$_3$) and that of (+)-ethyl 3-(4-chlorophenyl)-3-caproyloxypropionate was $[\alpha]_D$−11.0°(c1.0, CDCl$_3$).

We claim:

1. A method for producing an optically active alkyl 3-aryl-3-hydroxypropionate which comprises reacting, in the presence of esterase produced by a micro-organism or esterase obtained from an animal, a triglyceride with an alkyl 3-aryl-3-hydroxypropionate represented by the general formula:

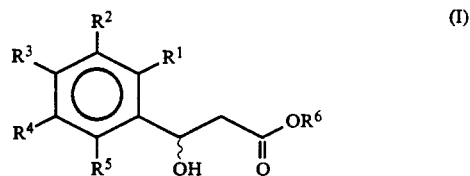

wherein $R^1$, $R^2$, $R^3$, $R^4$ and $R^5$ are hydrogen, hydroxyl, alkoxy of 1–4 carbon atoms, benzyloxy, fluorine, chlorine, or bromine and $R^6$ is alkyl, to effect a transesterification reaction, and resolving to an optically active alkyl 3-aryl-3-hydroxypropionate represented by the general formula:

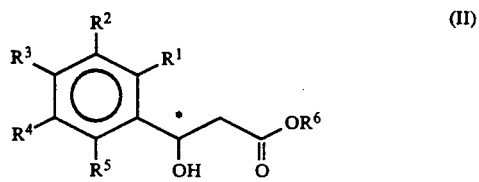

wherein $R^1$, $R^2$, $R^3$, $R^4$, $R^5$ and $R^6$ have the same meanings as described above, and an optically active alkyl 3-aryl-3-acyloxy propionate.

2. A method for producing an optically active alkyl 3-aryl-3-hydroxypropionate which comprises reacting in the presence of esterase produced by a micro-organism or esterase obtained from an animal, a fatty acid vinyl ester and an alkyl 3-aryl-3-hydroxypropionate represented by the general formula:

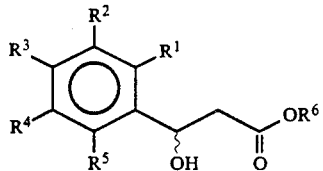

(I)

wherein $R^1$, $R^2$, $R^3$, $R^4$ and $R^5$ are hydrogen, hydroxyl, alkoxy of 1-4 carbon atoms, benzyloxy, fluorine, chlorine, or bromine and $R^6$ is alkyl, to effect a transesterification reaction, and resolving to an optically active alkyl 3-aryl-3-hydroxypropionate represented by the general formula:

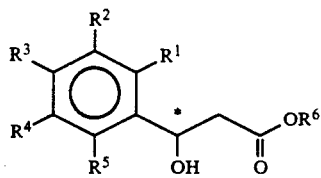

(II)

wherein $R^1$, $R^2$, $R^3$, $R^4$, $R^5$ and $R^6$ have the same meanings as described above, and an optically active alkyl 3-aryl-3-acyloxy propionate.

* * * * *